(12) United States Patent
Lange et al.

(10) Patent No.: US 7,664,300 B2
(45) Date of Patent: Feb. 16, 2010

(54) UTERINE CERVICAL CANCER COMPUTER-AIDED-DIAGNOSIS (CAD)

(75) Inventors: Holger Lange, San Diego, CA (US);
Rolf Holger Wolters, Kailua, HI (US)

(73) Assignee: STI Medical Systems, LLC, Honolulu, HI (US)

( * ) Notice: Subject to any disclaimer, the term of this patent is extended or adjusted under 35 U.S.C. 154(b) by 1036 days.

(21) Appl. No.: 11/184,046

(22) Filed: Feb. 3, 2005

(65) Prior Publication Data
US 2009/0046905 A1 Feb. 19, 2009

(51) Int. Cl.
*G06K 9/00* (2006.01)
*A61F 6/14* (2006.01)
*A61F 6/06* (2006.01)

(52) U.S. Cl. .................. 382/128; 128/841; 424/430

(58) Field of Classification Search ............. 382/128, 382/129, 130, 131, 132, 133, 134, 294, 190; 378/4, 21, 23–27, 901; 600/300, 411, 425, 600/427, 431; 607/901; 128/841; 436/64, 436/813; 424/430, 559
See application file for complete search history.

(56) References Cited

U.S. PATENT DOCUMENTS

| | | | | |
|---|---|---|---|---|
| 6,026,323 A * | 2/2000 | Skladnev et al. | ............ | 600/547 |
| 6,671,540 B1 * | 12/2003 | Hochman | ............ | 600/431 |
| 6,975,899 B2 * | 12/2005 | Faupel et al. | ............ | 600/476 |
| 7,127,282 B2 * | 10/2006 | Nordstrom et al. | ............ | 600/477 |
| 7,236,815 B2 * | 6/2007 | Richards-Kortum et al. | | 600/407 |

OTHER PUBLICATIONS

Ferris, Daron G.; Cox, J. Thomas; O'Connor, Dennis M.; Wright, V. Cecil and Foerster, John, Modern Colposcopy Textbook and Atlas, Chapter 8, Normal and Abnormal Colposcopic Features, Kendall/Hunt Publishing Company, Iowa 2004, pp. 175-191.

(Continued)

*Primary Examiner*—Abolfazl Tabatabai
(74) *Attorney, Agent, or Firm*—Martin Hsia

(57) ABSTRACT

Uterine cervical cancer Computer-Aided-Diagnosis (CAD) according to this invention consists of a core processing system that automatically analyses data acquired from the uterine cervix and provides tissue and patient diagnosis, as well as adequacy of the examination. The data can include, but is not limited to, color still images or video, reflectance and fluorescence multi-spectral or hyper-spectral imagery, coherent optical tomography imagery, and impedance measurements, taken with and without the use of contrast agents like 3-5% acetic acid, Lugol's iodine, or 5-aminolevulinic acid. The core processing system is based on an open, modular, and feature-based architecture, designed for multi-data, multi-sensor, and multi-feature fusion. The core processing system can be embedded in different CAD system realizations. For example: A CAD system for cervical cancer screening could in a very simple version consist of a hand-held device that only acquires one digital RGB image of the uterine cervix after application of 3-5% acetic acid and provides automatically a patient diagnosis. A CAD system used as a colposcopy adjunct could provide all functions that are related to colposcopy and that can be provided by a computer, from automation of the clinical workflow to automated patient diagnosis and treatment recommendation.

9 Claims, 6 Drawing Sheets

OTHER PUBLICATIONS

Sellors, John W. and Sankaranarayanan, R., Colposcopy and Treatment of Cervical Intraepithelial Neoplasia: A Beginners' Manual, Chapter 1, An introduction to the anatomy of the uterine cervix, International Agency for Research on Cancer, Lyon, France 2003, pp. 1-12.

Apgar, Barbara S, Brotzman, Gregory L., Spitzer, Mark, Colposcopy Principles and Practice An Integrated Textbook and Atlas, Chapter 6, Normal Transformation Zone, W.B. Saunders Company, Pennsylvania 2002, pp. 147-158.

* cited by examiner

UTERINE CERVICAL CANCER COMPUTER-AIDED-DIAGNOSIS (CAD)

FIELD OF INVENTION

This invention generally relates to medical imaging. The invention relates more specifically to the computer aided diagnosis of uterine cervical cancer.

BACKGROUND OF THE INVENTION

Uterine cervical cancer is the second most common cancer in women worldwide, with nearly 500,000 new cases and over 270,000 deaths annually (http://www-depdb.iarc.fr/globocan2002.htm; Ferlay J, Bray F, Pisani P, Parkin D M, eds. Globocan 2000: Cancer incidence, Mortality and Prevalence Worldwide, Version 1.0. IARC CancerBase No. 5. IARC Press; 2001; Pisani P, Parkin D M, Ferlay J. Estimates of the worldwide mortality from eighteen major cancers in 1985. Implications for prevention and projections of future burden. Int J Cancer 1993; 55:891-903). Because invasive disease is preceded by pre-malignant Cervical Intraepithelial Neoplasia (CIN), if detected early and treated adequately, cervical cancer can be universally prevented (Ferris D G, Cox J T, O'Connor D M, Wright V C, Foerster J. Modern Colposcopy, Textbook and Atlas, 2nd Edition. Kendall Hunt, Dubuque, Iowa, 2004). While almost 80% of the cases occur in developing countries where regular screening is unavailable or underutilized (Parkin, D. M., F. I. Bray and S. S. Devesa, Cancer burden in the year 2000. The global picture, Eur J Cancer 37 Suppl 8: S4-66, 2001), there are nearly 15,000 new cases diagnosed and 6,000 deaths annually in the United States (US) and Canada. In the US each year approximately 50 million women undergo cytological screening (Wright, T. C., Jr., J. T. Cox, L. S. Massad, L. B. Twiggs and E. J. Wilkinson, 2001 Consensus Guidelines for the management of women with cervical cytological abnormalities, Jama 287 (16): 2120-9, 2001), with some 7% (3.5 million) requiring additional follow-up (Jones, B. A. and D. D. Davey, Quality management in gynecologic cytology using interlaboratory comparison, Arch Pathol Lab Med 124(5): 672-81, 2000; Jones, B. A. and D. A. Novis, Follow-up of abnormal gynecologic cytology: a college of American pathologists Q-probes study of 16132 cases from 306 laboratories, Arch Pathol Lab Med 124(5): 665-71, 2000). It is estimated that the cost for colposcopic follow up and interventional treatment of abnormal cytological screening approaches 6 billion dollars annually in the US (Kurman, R. J., D. E. Henson, A. L. Herbst, K. L. Noller and M. H. Schiffman, Interim guidelines for management of abnormal cervical cytology, The 1992 National Cancer Institute Workshop, Jama 271(23): 1866-9, 1994).

Prophylactic Human Papillomavirus (HPV) vaccines, currently under development, have the potential to prevent cervical cancer. HPV is necessary, but not sufficient alone, for the development of cervical cancer. A monovalent HPV type 16 vaccine has been shown to be both safe and effective in preventing HPV type 16 cervical infections and HPV 16-related cervical cancer precursors (Koutsky L, Ault K A, Wheeler C M, Brown D R, Barr E, Alvarez F B, et al. A controlled trial of a human papillomavirus type 16 vaccine. N Engl J Med 2002; 347:1645-51). Bivalent (HPV types 16 and 18) HPV vaccines could prevent 75% of all cervical cancers (Harper, D. M., E. L. Franco, C. Wheeler, D. G. Ferris, D. Jenkins, A. Schuind, T. Zahaf, B. Innis, P. Naud, N. S. De Carvalho, C. M. Roteli-Martins, J. Teixeira, M. M. Blatter, A. P. Korn, W. Quint, and G. Dubin, Efficacy of a bivalent L1 virus-like particle vaccine in prevention of infection with human papillomavirus types 16 and 18 in young women: a randomised controlled trial. Lancet, 2004. 364(9447): p. 1757-65). However, these vaccines will not be commercially available for at least 3 to 5 years. Further, they will not prevent all cases of cervical cancer. Because vaccination should occur prior to initiating sexual intercourse, it may be 60 years before the risk to various populations will be effectively reduced. The cost of the vaccine will also be substantial, perhaps equivalent to that for Hepatitis B vaccine. The poor and geographically isolated, who are at greatest risk for cervical cancer, may not benefit at all.

Colposcopy is the primary diagnostic method used in the US to detect CIN and cancer, following an abnormal cytological screen (Papanicolaou smear). The purpose of a colposcopic examination is to identify and rank the severity of lesions, so that biopsies representing the highest-grade abnormality can be taken, if necessary. A colposcopic examination involves a systematic visual evaluation of the lower genital tract (cervix, vulva and vagina), with special emphasis on the subjective appearance of metaplastic epithelium comprising the transformation zone on the cervix. For this purpose an optical colposcope is used, which has been in use for almost 80 years. A colposcope is a low powered binocular microscope with a built in white light source and objective lens attached to a support mechanism (B. S. Apgar, Brotzman, G. L. and Spitzer, M., Colposcopy: Principles and Practice, W.B. Saunders Company: Philadelphia, 2002). A green filter may be used to accentuate vasculature. During the exam, a 3-5% acetic acid solution is applied to the cervix, causing abnormal and metaplastic epithelia to turn white. Cervical cancer precursor lesions and invasive cancer exhibit certain distinctly abnormal morphologic features that can be identified by colposcopic examination (Stafl A, Mattingly R F. Colposcopic diagnosis of cervical neoplasia. Obstet Gynecol 1973; 41:168-76; Coppelson M, Dalrymple J C, Atkinson K H. Colposcopic differentiation of abnormalities arising in the transformation zone. Contemp Colposcopy 1993; 20:83-110; Reid R, Krums E P, Herschman B R, et al. Genital warts and cervical cancer V. The tissue basis of colposcopic change. Am J Obstet Gynecol 1984; 149:293-303; Benedet J L, Anderson G H, Boyes D A. Colposcopic diagnosis of invasive and occult carcinoma of the cervix. Obstet Gynecol 1985; 65:557-562). Lesion characteristics such as margin shape; color or opacity; blood vessel caliber, intercapillary spacing and distribution; and contour are considered by physicians (colposcopists) to derive a clinical diagnosis (Reid R, Scalzi P. Genital warts and cervical cancer. VII An improved colposcopic index for differentiating benign papillomaviral infection from high-grade cervical intraepithelial neoplasia. Am J Obstet Gynecol 1985; 153:611-618). These colposcopic signs, when considered aggregately, determine the severity of the neoplasia and discriminate abnormal findings from similarly appearing, anatomically normal variants. Various colposcopic indices, based on grading lesion characteristics, provide clinicians structured approaches to predicting histologic findings (Stafl A, Mattingly R F. Colposcopic diagnosis of cervical neoplasia. Obstet Gynecol 1973; 41:168-76; Coppelson M, Dalrymple J C, Atkinson K H. Colposcopic differentiation of abnormalities arising in the transformation zone. Contemp Colposcopy 1993; 20:83-110; Reid R, Krums E P, Herschman B R, et al. Genital warts and cervical cancer V. The tissue basis of colposcopic change. Am J Obstet Gynecol 1984; 149:293-303). However, due to the subjective nature of the examination, the accuracy of colposcopy is highly dependent upon colposcopist experience and expertise. Even in expert hands, colposcopy suffers from low specificity leading to many unnecessary biopsies (Mikhail, M. S., I. R. Merkatz and S. L. Romney, Clinical usefulness of computerized colposcopy: image analysis and conservative management of mild dysplasia, Obstet Gynecol 80(1): 5-8, 1992). These avoidable biopsies cause an increased risk of infection, patient discomfort, delayed treatment and substantially increased costs.

Digital imaging is revolutionizing medical imaging and enabling sophisticated computer programs to assist the physicians with Computer-Aided-Diagnosis (CAD). Clinicians and academia have suggested and shown proof of concept to use automated image analysis of cervical imagery for cervical cancer screening and diagnosis. In one study, a computer system demonstrated greater agreement rates with histologic diagnoses (85%, k=0.77) than did colposcopists' impressions (66%, k=0.40) (Craine B L, Craine E R. Digital imaging colposcopy; basic concepts in applications. Obstet Gynecol 1993; 82:69-73). In another, the computer system was readily able to discriminate CIN 3 from normal epithelium and immature metaplasia (Eillen D. Dickman, Theodore J. Doll, Chun Kit Chiu, and Daron G. Ferris, Identification of Cervical Neoplasia Using a Simulation of Human Vision, Journal of Lower Genital Tract Disease, Vol. 5, No. 3, 2001, pp 144-152). One computer system for colposcopy has also demonstrated an ability to serially monitor untreated low grade lesions for evidence of progression or regression (Mikhail M S, Merkatz I R, Rommey S L. Clinical usefulness of computerized colposcopy: Image analysis and conservative management of mild dysplasia. Obstet Gynecol 1992; 80:5-8). Since intercapillary distances increase proportionally with disease severity, another computer system was able to measure these tiny distances to successfully predict the specific level of cervical neoplasia (Mikhail M S, Romney S L. Computerized measurement of intercapillary distance using image analysis in women with cervical intraepithelial neoplasia: correlation with severity. Obstet Gynecol 2000; 95:52-3).

Various image processing algorithms have been developed to detect different colposcopic features. At the University of New South Wales (UNSW), Australia, Van Raad developed algorithms to detect the transformation zone using an active contours model (snakes) at multiple scales (Viara Van Raad, Active Contour Models—A Multiscale Implementation for Anatomical Feature Delineation in Cervical Images; Proceedings of the IEEE International Conference of Image Processing—ICIP 2004, Oct. 24-27, pp. 557-560, 2004; Van Raad, V. and Bradley A.; Active contour model based segmentation of colposcopy images from cervix uteri using Gaussian Pyramids; Proceedings of the 6th International Symposium on DSP and Communication Systems. 133-138, January 2002) and a novel wavelet-based algorithm looking at local frequency content (V. Van Raad; A Novel Wavelet-based Image Analysis Algorithm for Detection of Important Anatomical Features in Colposcopy Image; Proceedings of ICBME'02. 61-62, December 2002). Yang et al., at Texas Tech University, developed a segmentation algorithm to detect acetowhite epithelium using a statistical optimization scheme (deterministic annealing) for accurate clustering to track the boundaries of the acetowhite regions (Yang S., Guo J., King P., Sriraja Y., Mitra S., Nutter B., Ferris D., Schiffman M., Jeronimo J., and Long R.; A multi-spectral digital cervigram™ analyzer in the wavelet domain for early detection of cervical cancer; Proceedings of SPIE on Medical Imaging, Vol. 5370 Bellingham, Wash. 2004, pages 1833-1844). Gordon and coworkers, at Tel-Aviv University, developed a segmentation algorithm for three tissue types in cervical imagery (original squamous, columnar, and acetowhite epithelium) based on color and texture information (Gordon S., Zimmerman G., and Greenspan H.; Image segmentation of Uterine Cervix images for indexing in PACS; Proceedings of the 17$^{th}$ IEEE Symposium on Computer-Based Medical Systems (CBMS'04), 2004). The set of regions in the images was represented by a Gaussian mixture model, while an Expectation-Maximization algorithm was used to determine the maximum likelihood parameters of the statistical model in the feature space. As a result, the labeling of a pixel could be affiliated with the most probable Gaussian cluster according to Bayes rule. Ji et al (Qiang Ji, John Engel, and Eric Craine, Texture Analysis for classification of Cervix Lesions, IEEE Transactions on Medical Imaging, Vol. 19, No. 11, November 2000, pp 1144-1149; Qiang Ji, John Engel, and Eric Craine, Classifying cervix tissue patterns with texture analysis, Pattern Recognition, Vol. 33, 1561-1573) presented a generalized texture analysis algorithm for classifying the vascular patterns from colposcopic images. They investigated six characteristic pathological vascular patterns, including network capillaries, hairpin capillaries, two types of punctation vessels and two types of mosaic vessels. Others have applied a combination of conventional statistical and structural texture analysis approaches. For example, Balas (Costas Balas, *A novel optical imaging method for the early detection, quantitative grading, and mapping of cancerous and precancerous lesions of cervix*, IEEE Transactions on Biomedical Engineering, Vol. 48, No. 1, January 2001, 96-104) and Orfanoudaki et al. (Irene M. Orfanoudaki, G. C. Themelis, S. K. Sifakis, D. H. Fragouli, J. G. Panayiotides, E. M. Vazgiouraki, E. E. Koumantakis, *A clinical study of optical biopsy of the uterine cervix using a multispectral imaging system*, Gynecologic Oncology, Vol. 96, 2005, 119-131) analyzed the temporal decay of the acetic acid whitening effect by measuring the intensity profile over time. Furthermore, several approaches for tissue classification have been developed: a simple colposcopic image classification method by artificial neural network using the lesion contour features (I. Claude, R. Winzenrieth, P. Pouletaut, and J. C. Boulanger, Contour Features for colposcopic image classification by artificial neural networks, in Proceedings of international conference on Pattern Recognition, 2002, 771-774), a rule based medical decision support system for detecting different stages of cervical cancer based on the signs and symptoms from physical examination (Pabitra Mitra, Sushmita Mitra, and Sankar K. Pal, Staging of Cervical Cancer with Soft Computing, IEEE Transactions on Biomedical Engineering, Vol. 47, No. 7, July 2000, pp 934-940), the classification of cervical tissue based on spectral data using multi-layered perceptrons and Radial Basis Function (RBF) networks (Kagan Tumer, Nirmala Ramanujam, Joydeep Ghosh, and Rebecca Richards-Kortum, Ensembles of Radial Basis Function Networks for Spectroscopic Detection of Cervical Precancer, IEEE Transactions on Biomedical Engineering, Vol. 45, No. 8, August 1998) and multivariate stochastic training algorithms (A. K. Dattamajumdar, D. Wells, J. Parnell, J. T. Lewis, D. Ganguly and T. C. Wright Jr., Preliminary experimental results from multi-center clinical trials for detection of cervical precancerous lesions using the Cerviscan™ system: a novel full field evoked tissue fluorescence based imaging instrument, in Proceedings of the 23rd Annual EMBS international conference, October 25-28, Istanbul, Turkey, pp 3150-3152).

CAD for colposcopy could have a direct impact on improving women's health care and reducing associated costs. A product realization where a CAD system is incorporated into a low-cost hand-held device, creating in effect a machine expert colposcopist, could improve screening cost-effectiveness in developing countries. Similarly, a product realization, where a CAD system operates as an adjunct to colposcopy could minimize the high variability among colposcopists and establish a consistent, higher standard for accuracy. Consequently, fewer false-positive biopsies or ultimately no biopsies would be required.

SUMMARY OF THE INVENTION

This invention provides systems and methods for a processing system that automatically analyzes data acquired from the uterine cervix and provides tissue and patient diagnosis, as well as adequacy of the examination.

The invention separately provides systems and methods for a Computer-Aided-Diagnosis (CAD) system for cervical cancer screening.

The invention separately provides systems and methods for a Computer-Aided-Diagnosis (CAD) system as colposcopy adjunct.

The invention separately provides systems and methods to acquire, visualize and analyze 3D topology data from the uterine cervix.

The invention separately provides systems and methods to provide the physician with example data of reference lesions (cervix) including their diagnosis from a reference database.

These and other features and advantages of this invention are described in or are apparent from the following detailed description of the preferred embodiments.

BRIEF DESCRIPTION OF THE DRAWINGS

The preferred embodiments of this invention will be described, with reference to the following figures, wherein.

DETAILED DESCRIPTION OF PREFERRED EMBODIMENTS

Computer-Aided-Diagnosis (CAD) Processing System

Figure 1:
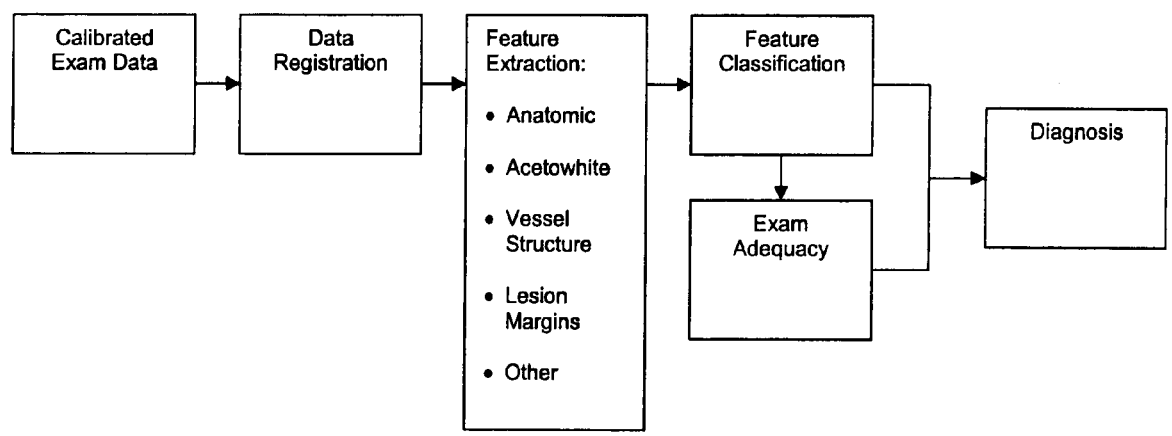
FIG. 1 illustrates the processing system of a uterine cervical cancer CAD system.

This invention provides systems and methods for a processing system that automatically analyzes data acquired from the uterine cervix and provides tissue and patient diagnosis, as well as adequacy of the examination.

The system takes calibrated (gray balance, color calibration, etc.) data of the cervical examination as input and provides as output the detected features and their classification, the tissue diagnosis for all locations on the cervix and an assessment of the examination adequacy. Calibration parameters (pixel size, etc.), demographic parameters (age, pregnancy, etc.), patient history (screening result, etc.) and system parameters (sensitivity, etc.) are used as the parameters of the system. The system architecture is open, modular, and feature-based. It is designed for multi-data (different moments in time, different contrast agents like acetic acid, Lugol's iodine, 5-aminolevulinic acid, etc.), multi-sensor (RGB still/video camera with white light, 3D data acquisition system, hyper-/multi-spectral camera with white and/or UV light, impedance acquisition system, etc.), and multi-feature (colposcopic features, feature from new instrument technologies, other plausible features that can be extracted from the data, etc.) fusion. The architecture identifies three basic processing layers: (1) data registration, (2) feature extraction and (3) feature classification. In the data registration layer, all calibrated exam data gets spatially registered to a selected reference image. This is necessary so that all extracted features can be fused in the feature classification layer and feature extraction modules can exchange data between them. The feature extraction layer is divided into distinct modules by evaluating distinct anatomical and physiological phenomenology for each module. Each feature extraction module can use any of the registered data sources for processing, and also, data can be exchanged among modules. Furthermore, each feature extraction module can fuse different algorithms that redundantly extract the same feature parameters to improve performance. The feature classification layer consists of the tissue diagnosis module that provides the classification of each individual feature and combines the outputs of all feature extraction modules in order to determine the tissue diagnosis for all locations on the cervix, and the determination of the adequacy of the exam. The exam adequacy determination can be based on its own specific feature extraction modules and/or the feature parameters from other feature extraction modules. Different instruments provide different data sets, implying that different feature sets will be calculated depending on the instrument used. For simplicity, feature extraction modules should be designed to depend only on one data source and only to use data from other feature extraction modules that use the same data source as input. Nevertheless, the fusion of different data sources to extract specific features should be done at the feature extraction layer and not carried over into the feature classification layer. So, feature extraction modules that use different data sources and data from other feature extraction modules that use different data sources should be designed with this in mind so that they work under all possible data source combinations! Because the tissue diagnosis system performance is dependent on the fusion of all available features, the system is designed so that it can be trained automatically for any combination of features.

FIG. 1 illustrates the processing system of a uterine cervical cancer CAD system.

The core system (in gray) consists of the extraction of the anatomic features and the three most important colposcopic features: acetowhite, vessel structure, and lesion margins; the determination of the adequacy of the exam, and the tissue diagnosis. It uses only one RGB color image as input, therefore, by definition, this should be the reference image and no data registration is required. The RGB color image should have been taken with cross-polarization to eliminate the glare and at sufficient resolution to resolve the blood vessel structures. The RGB color images should at least be gray balanced and color calibrated and the size of the pixels be known from a camera calibration. The reference image should be taken at the moment in time after application of 3-5% acetic acid when the acetowhite effect is still visible and the blood vessels can be seen again (blood vessels are difficult to be seen right after the application of acetic acid). This is a compromise for the acetowhite and vessel structure feature extraction modules. When more images become available after application of acetic acid, the acetowhite and vessel structure feature extraction modules should each use the most appropriate image as their input to optimize performance. The temporal decay of acetowhite feature parameter cannot be assessed with one image alone and is therefore identified as a separate feature extraction module that requires a series of images after application of acetic acid. The contour (3D topology) feature as well cannot be assessed with one cross-polarized image alone and is therefore identified as a feature extraction module that needs additional data. The Lugol's iodine feature is also considered an extension of the core system as an image with Lugol's iodine as contrast agent needs to be acquired.

Any extension of the feature set will lead to improved system performance. The core system can be extended with the extraction of other colposcopic findings that will have an impact on the tissue diagnosis. Some of the other colposcopic findings (e.g. endocervical polyps) can be assessed using the same reference image, while others (e.g. keratosis) might require additional data. In general, any other plausible feature, like texture analysis, that can be extracted from the data sources can be added to the system.

Additional features can be added to the system as data from new instrument technologies becomes available, such as fluorescence hyper- or multi-spectral imaging spectroscopy, 3D data acquisition systems, or impedance acquisition systems. However, when more than one image is used as input, all data needs to be registered to the reference image. Note that the cervix undergoes soft-tissue movements and that when data has been acquired at different moments in time, the registration algorithms need to account for this kind of movement. Image registration algorithms must also accommodate common "contaminants" such as blood, mucus and debris. There are several different types of data that need to be registered against the reference image. Multi-data registration of an acetowhite decay sequence against the reference image seems to be the easiest registration problem, as the reference image is one of the images in the sequence, and the acetowhite effect only changes slightly from image to image. However, it is a significantly more challenging task to register not only multi-data, but also multi-exam data, to the pixel level when images taken several months apart, as envisioned by some to detect lesion changes over time. In this case, the appearance of the cervix can change considerably over such a long timeframe. One approach to this problem is to register multi-exam data at a higher processing level, such as at the level of the diagnosed lesions. Currently, we consider this function to be performed outside the processing system using its output from the tissue diagnosis. The multi-data registration of images taken with no contrast agent, like an image taken prior to the acetic acid application, or different contrast agents, like Lugol's iodine, against the reference image might also be very challenging. The images look very different due to the different effects of the contrast agents, the fact that the cervix has been manipulated during the application of the contrast agent, and the fact that the instrument might have moved. An image taken prior to the acetic acid application, without the acetowhitening effect present, would be the best data source for the detection of blood vessel structures and keratosis. To work around the registration problem, we can use an image taken long time after the application of acetic acid instead where the acetowhite effect has faded considerably. For the multi-sensor registration of data acquired by different sensors, like 3D acquisition systems and fluorescence hyper-/multi-spectral imaging systems, a reflectance image that is spatially correlated to the sensor data needs to be provided so that this image can be registered against the reference image. This task is simplified by acquiring the data from different sensors close to the moment in time when the reference image is taken. We have previously described a means to embed (and thereby register) a reflectance image in fluorescence hyperspectral data, when the acquisition of the reflectance and fluorescence data cannot be interleaved (Lange, H., Baker R., Håkansson J., Gustafsson U.; Reflectance and fluorescence hyperspectral elastic image registration; SPIE Medical Imaging 2004; SPIE Proc. 5370, 2004).

3D Cervix Topology

The invention provides systems and methods to acquire and analyze 3D topology data from the uterine cervix.

The contour feature presents a special problem, as a colposcopist uses the glare pattern associated with surface relief, stereoscopic view and the movement of the colposcope for its assessment. For the digital colposcopy system, we use 3D reconstruction to assess the contour feature. A 3D reconstruction system can be implemented in different ways, including: add a non-polarized image to use shape from shading, add an image from a different view point (stereoscopic view) to use stereovision (combined with shape from shading), acquire images taken with special light patterns (Moire, structured light, etc.) projected onto the cervix to reconstruct the 3D surface, or use laser range finders. The 3D topology of the cervix can also be used for precise measurements of lesions to follow their progression over multiple exams.

Computer-Aided-Diagnosis (CAD) System Cervical Cancer Screening

The invention provides systems and methods for a Computer-Aided-Diagnosis (CAD) system for cervical cancer screening.

The processing system can be embedded into an instrument for cervical cancer screening.

In a very simple configuration for example, one digital RGB image of the uterine cervix is acquired after application of 3-5% acetic acid and automatically the patient diagnosis is provided. The processing system could incorporate algorithms to detect and analyze the three most important colposcopic features: (1) acetowhite epithelium, (2) vessel structure, and (3) lesion margins. The flexible design of the processing system enables progressive performance enhancements at later stages as new component algorithms are added to detect other features (e.g. contours, texture), epithelial contrast agents (e.g. Lugol's iodine solution, 5-AminoLevulinic Acid (ALA)), or sensors (e.g. fluorescence imaging spectroscopy). The data input to the processing system would be a gray balanced and color-calibrated, cross-polarized (no glare) digital RGB color image of the cervix after application of 3-5% acetic acid. The system parameters could include an adjustable system sensitivity parameter and the demographic input parameters, age (>40 years) and Last Menstrual Period (LMP) (>30 days). The system could consist of six image processing algorithms: (1) anatomy feature detection, (2) acetowhite feature detection and characterization, (3) vessels feature detection and characterization, (4) lesion margin feature detection and characterization, (5) examination adequacy calculation and (6) tissue classification. The CAD system output could provide a diagnostic exam result (normal/low-grade, high-grade dysplasia, or cancer), and a binary exam adequacy result (satisfactory/unsatisfactory).

Figure 2:
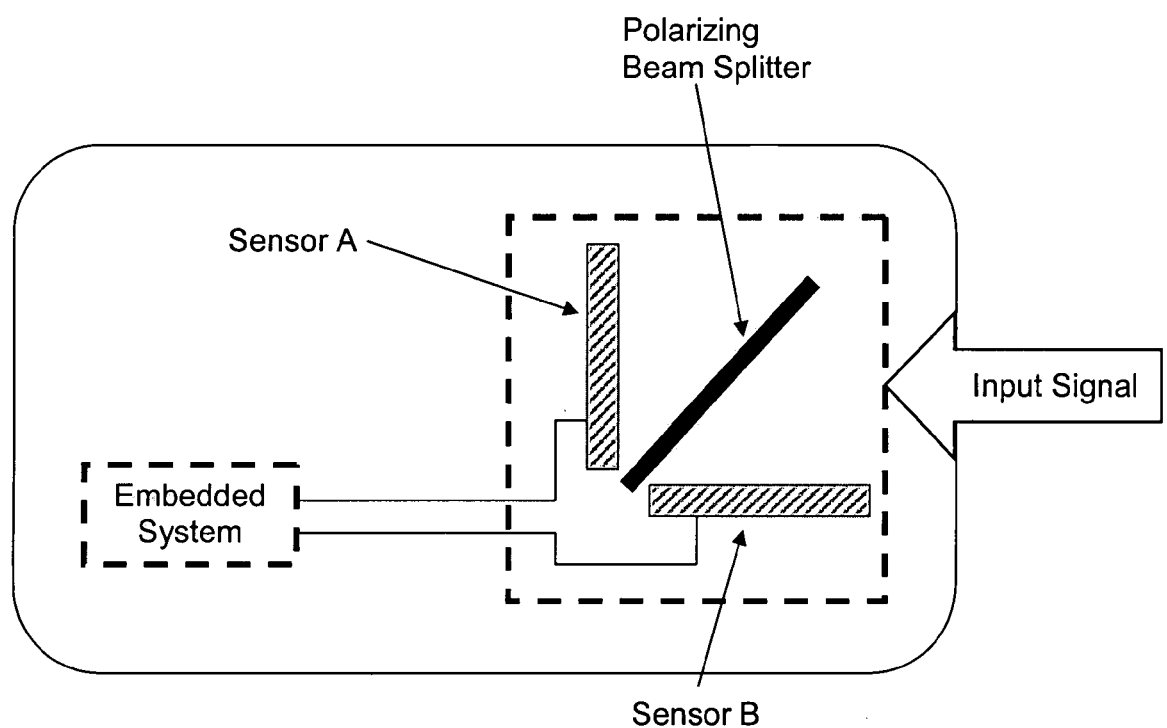
FIG. 2 shows an artist's impression of the screening instrument.

FIG. 2 shows an artist's impression of the screening instrument.

The screening instrument incorporates a digital camera with embedded processing, an illumination source and flash, and battery pack. The functionality of the instrument hardware prototype is similar to the "Cerviscope®" camera manufactured by National Testing Laboratories (NTL). The Cerviscope is a customized hand-held camera that uses 35 mm film to acquire cervical images. However, Cerviscope results are not immediately available because the film must be mailed to distant centers, developed, and the images interpreted by NTL. The screening instrument differs from, and we believe improves upon, the Cerviscope in two important ways. First, the screening instrument will produce high-quality, calibrated digital images, rather than use film. Secondly, the system will have embedded processing for instant colposcopic analysis by the CAD system.

The digital camera component can consist of a commercial camera, a camera kit, or other forms of data acquisition systems. The digital camera component interfaces to an embedded processing platform. The digital camera component can consist of a RISC and Digital Signal Processors (DSP) with FLASH and RAM memories, Multimedia processors, FPGAs, reconfigurable logic or other embedded processing resources.

Figure 3:
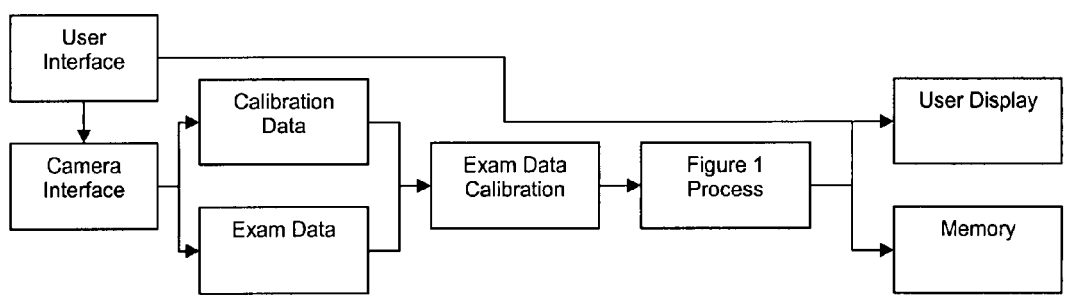
FIG. 3 shows the instrument and software overview of the screening instrument.

FIG. 3 shows the instrument and software overview of the screening instrument.

Figure 4:
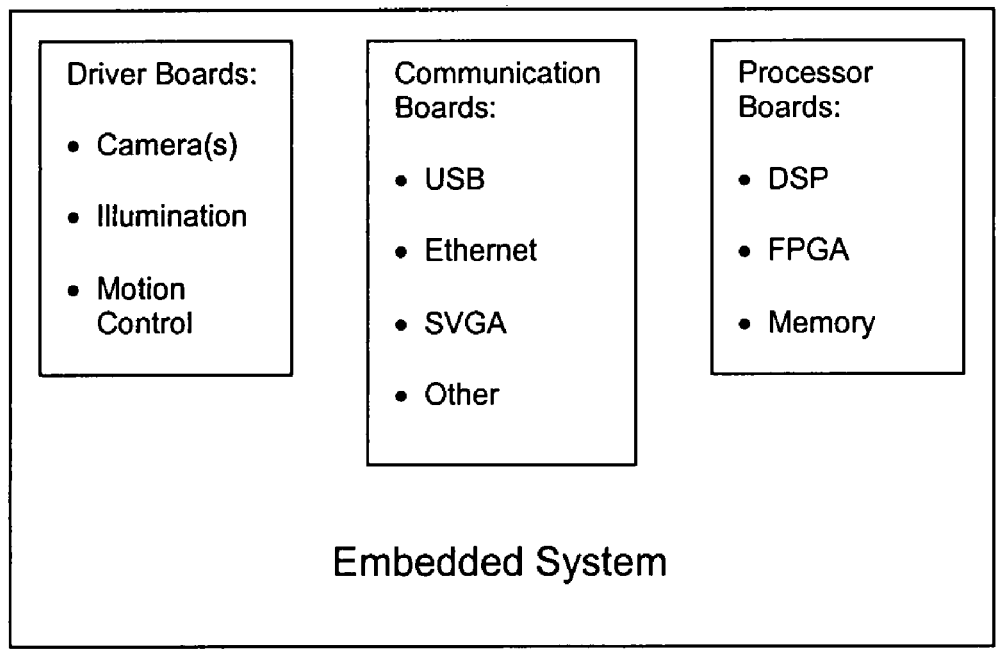
FIG. 4 shows the hardware overview of the screening instrument.

FIG. 4 shows the hardware overview of the screening instrument.

More complex processing system configurations, as outlined above, can be embedded into more complex screening instruments.

Computer-Aided-Diagnosis (CAD) System as Colposcopy Adjunct

The invention provides systems and methods for a Computer-Aided-Diagnosis (CAD) system as colposcopy adjunct.

A CAD system as a colposcopy adjunct includes all functions that are related to colposcopy and that can be provided by a computer, from automation of the clinical workflow to automated patient diagnosis and treatment recommendation. The CAD system is a software program that may run on various processing platforms such as computers, DSP/FPGA processing boards, embedded systems, etc., and that interfaces to a cervical data acquisition system such as a digital colposcope, video colposcope, optical colposcope with camera, film based camera with scanner, digital camera, etc.

Figure 5:
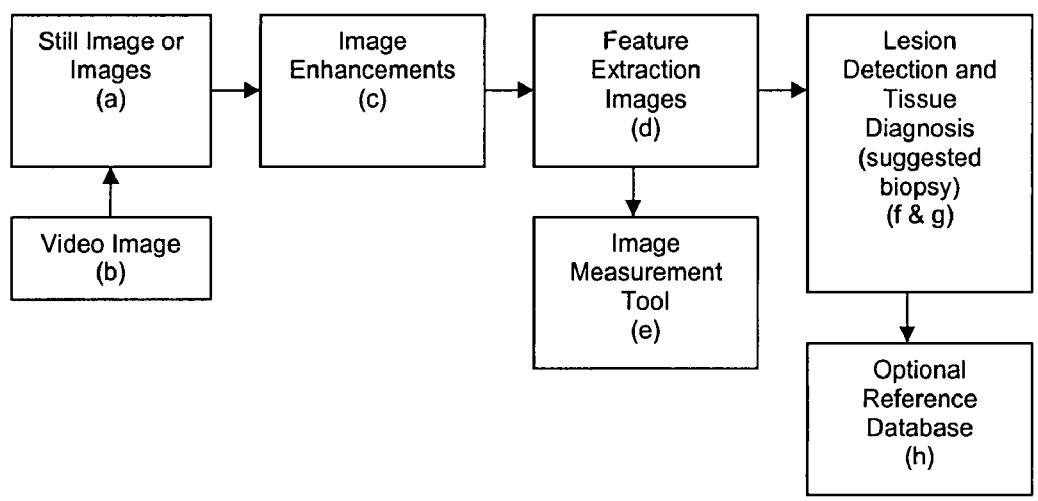
FIG. 5 shows rendered views of a CAD system as colposcopy adjunct.

FIG. 5 shows a function diagram of a CAD system as colposcopy adjunct. (a) High-resolution still images from the examination can be displayed to the physician on a high-resolution monitor; (b) Live video of the examination can be viewed and replayed; (c) Images and video can be enhanced using image enhancement such as glint removal, and green filter; (d) Automated extraction and display of diagnostic features such as acetowhite region, vessel structure, lesion margins, acetowhite decay, and contour. These can be displayed to the physician either in an overview or individually; (e) Feature measurements can be provided to the physician on demand; (f) Automated lesion detection and tissue diagnosis can be indicated to the physician; (g) Suggested biopsy sites can be indicated to the physician; and (h) Reference images of similar lesions and their characteristics can be brought up from a reference database and shown to the physician for comparison.

The functions of a CAD system as colposcopy adjunct are comprised of the following components:
1. Modality Data Management System
2. Image Enhancement
3. Feature Extraction
4. Reference Database
5. Diagnosis and directed Biopsies Note that the order in which the functions are listed reflects the degree of assistance or automation in the patient diagnosis. Therefore, those functions can also be used to describe the diagnosis assistance or automation level performed by a CAD system.

Modality Data Management System

The Modality Data Management Systems (MDMS) provides a data management infrastructure for digital colposcopy. The MDMS can provide:
Management (storage, playback, etc.), display and annotation of the acquired data,
Automation of the workflow related to colposcopy, including:
Administration of the patient data and history,
Electronic forms (consent form, colposcopy form, etc.),
Patient education and information material (videos, etc.) and entertainment (TV, soap operas, etc.),
Colposcopy support material (cervical atlas, reference database, treatment guidelines, patient management recommendations, etc.),
Letter generation (follow up, etc.),
Documentation (results, follow up, etc.),
Interfaces and integration to
Picture Archiving and Communication System (PACS), Digital Imaging and Communication in Medicine (DICOM) is the standard defining the communication between a modality and a PACS system. Note that currently no specific DICOM standard for digital colposcopy exists. Once a couple of companies express interest in such standardization, a new DICOM standard for digital colposcopy can be defined.
Pathology laboratory,
Accounting system (billing) and
Telemedicine.

It is necessary to account for differences in data collection inherent to transitioning the colposcopic exam from an optical to a digital device. For example, changes in image resolution can be addressed by using a high-resolution still camera instead of video camera to provide high-resolution imagery.

A further practical issue in creating a MDMS is the need to make the computer in a physician's examination room available for universal use. The computer cannot be limited to one modality, but rather needs to be able to support the automation of the entire workflow and all modalities in a practice. This also means that the CAD system for colposcopy needs to integrate well with other workflow automation and modality support applications.

Today, colposcope manufacturers provide only stand-alone image or video management systems as add-ons to their digital and video colposcopes.

Figure 6:
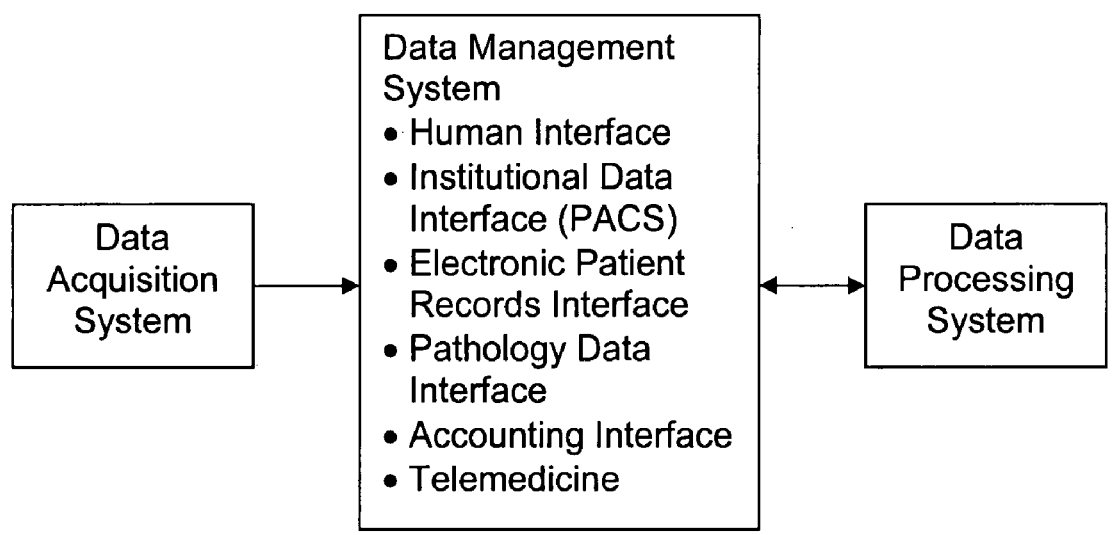
FIG. 6 shows a system overview of a Modality Data Management System for colposcopy.

FIG. 6 shows a system overview of a Modality Data Management System for colposcopy.

3D Cervix Topology

The invention provides systems and methods to acquire and visualize 3D topology data from the uterine cervix.

Cervical topological features can be visualized in the digital mode using 3D monitors with stereoscopic image/video feed or 3D digitization.

Image Enhancement

A "digital colposcope" can provide numerous image enhancements, including:
Green filter to accentuate vasculature, as used in almost all colposcopes.
The characteristics of the imagery can be changed so it appears to come from a different colposcope (and/or light source). Mapping the color-space of one colposcope to that of another can provide the same image appearance.

General image enhancements, like contrast, brightness, zoom, sharpening, etc. as can be found in standard commercial image processing packages like Photoshop®.

Glare removal to provide information in the image regions that are normally destroyed by glare. Note that the colposcopist uses glare patterns to assess the contour of the lesions (3D topology), therefore glare-free images should only be provided in addition to images with glare. Glare can be removed by designing the acquisition system with cross-polarization (preferred) or by software. Using software to remove the glare only allows interpolating the destroyed image regions, but does not recover the underlying information and may also introduce artifacts in the imagery by removing regions that are mistaken for glare.

3D topology-based illumination normalization to lighten up dark regions on the periphery of the cervix. 3D reconstruction of the cervix allows compensating for the differences in illumination due to the 3D topology of the cervix.

Feature Extraction

A colposcopist uses different features to assess the cervix; those features can automatically be extracted from the cervical data and shown to the colposcopist to help him in his assessment. A core feature set includes the visual features used by colposcopists. This feature set can be extended to include new features introduced by new instrument technologies, like fluorescence and impedance, and any other plausible feature that can be extracted from the cervical data.

Colposcopic features include:
  Anatomic
  Acetowhite
  Blood vessel structure
  Lesion margin
  Contour
  Lugol's iodine staining Images enhancements can be provided that enhance specific features in the imagery, in particular colposcopic features. The individual features can also be classified in terms of their significance to the tissue diagnosis: normal, low-grade, high-grade and cancer. The extracted and classified features can be presented to the colposcopist individually or combined as overlay on an image of the cervix (preferable a universal reference image—typically a color image after acetic acid application); similar to the colposcopic impression annotation. An overlay allows the colposcopist to relate the different extracted features back to their location on the cervix.

Companies developing new instrument technologies for detecting cervical neoplasia, such as we and others have done using fluorescence and reflectance spectroscopy (Ferris, D. G., R. A. Lawhead, E. D. Dickman, N. Holtzapple, J. A. Miller, S. Grogan, S. Bambot, A. Agrawal, and M. L. Faupel, Multimodal Hyperspectral Imaging for the Noninvasive Diagnosis of Cervical Neoplasia. Journal of Lower Genital Tract Disease, 2001. 5(2): p. 65-72; Huh, W. K., R. M. Cestero, F. A. Garcia, M. A. Gold, R. S. Guido, K. McIntyre-Seltman, D. M. Harper, L. Burke, S. T. Sum, R. F. Flewelling, and R. D. Alvarez, Optical detection of high-grade cervical intraepithelial neoplasia in vivo: results of a 604-patient study. Am J Obstet Gynecol, 2004. 190(5): p. 1249-57; Parker, M. F., G. C. Mooradian, J. P. Karins, D. M. O'Connor, B. A. Speer, P. D. Owensby, and A. Velasco, Hyperspectral Diagnostic Imaging of the Cervix: Report on a New Investigational Device. Journal of Lower Genital Tract Disease, 2000. 4(3): p. 119-124), typically introduce their technology as a separate stand-alone solution that provides only the specific feature they detect with their device.

Reference Database

The invention provides systems and methods to provide the physician with example data of reference lesions (cervix) including their diagnosis from a reference database.

A colposcopic diagnosis can be assisted, by providing, based on selected feature parameters, matching examples of reference lesions/cervixes including their diagnosis (and feature parameters). The key is to be able to characterize all lesions by their feature parameters. A reference database can be built up from cervical data sets (preferable LEEP specimens that have greater tissue coverage) for which the diagnosis and the feature parameters of all lesions are available. The ground truth for the diagnosis can be determined by expert colposcopists and pathologists. The feature parameters can as well be determined by expert colposcopists and pathologists or automatically be calculated by feature extraction algorithms. The search keys of the reference database are the feature parameters; a reference database search then provides matching examples. The search feature parameters can be input (or modified) manually or the feature parameters for a designated location or the highest grade lesion of the cervix under examination can be provided by the feature extraction algorithms. Bringing up examples of varied or different feature parameters than present in the current cervix under examination might also be helpful for the assessment.

Diagnosis and Directed Biopsies

Tissue diagnosis provides the colposcopist with the automated detection, localization and classification (in terms of severity: normal, low-grade, high-grade or cancer) of all lesions on the cervix. The classification results can be presented as overlay on an image of the cervix, preferable a universal reference image. Note that not one feature alone can provide reliable tissue diagnosis. All available features, starting with the obvious visual ones used by colposcopists, and adding those from new instrument technologies should be integrated into one system to optimize performance.

Automated assessment of the adequacy of the examination (visualization of the entire transformation zone) is also provided, as this affects patient management options.

The goal of colposcopy is to direct where biopsies should be taken. Based on the feature extraction and tissue diagnosis, the CAD system can determine the minimum number of biopsies needed, identify where these sites are located and display their locations as overlay on an image.

Ultimately, it is envisioned that the patient diagnosis can be derived directly from the computer's analysis, once clinical studies demonstrate sufficient performance compared to standard colposcopy and pathology.

The invention claimed is:

1. A process for diagnosing cancer in a cervix, comprising:
   obtaining a gray balanced and color calibrated reference single image of said cervix having known pixel sizes using a digital camera;
   spatially registering onto said single image of said cervix multiple calibrated data sets, each of said data sets being a different type of calibrated data which can be utilized for the detection of cervical cancer;
   applying at least two selected diagnostic algorithms to at least one of said multiple data sets to extract colposcopic features from said data sets to obtain classifications of said extracted features;
   combining classifications of said extracted features;
   assessing examination adequacy of said combined classifications; and if said examination adequacy is sufficient, determining tissue diagnosis;

whereby reliability of said tissue diagnosis is increased.

2. A process according to claim 1, wherein said different types of calibrated data include data selected from the group consisting of video or still images of fluorescence, reflectance, electrical impedance, or coherent optical tomography imagery.

3. A process according to claim 1, wherein said different types of calibrated data include data selected from the group consisting of multiple images taken over time, and multiple images taken from different examinations.

4. A process according to claim 1, wherein said diagnostic algorithms identify regions of colposcopic interest and are selected from the group consisting of acetowhite decay, vessel structure and lesion margins.

5. A process according to claim 1, further comprising:

displaying extracted and classified features as an overlay over said single image, whereby different extracted and classified features can be related back to their location on said cervix.

6. A process according to claim 1, wherein said applying step is performed by applying said at least two diagnostic algorithms only to one of said multiple data sets.

7. A process according to claim 1, wherein said obtaining step is performed by obtaining said single image of said cervix using cross polarization at sufficient resolution to resolve blood vessel structures after application of 3-5% acetic acid, which creates an acetowhite effect, when the acetowhite effect is still visible and blood vessels can be seen again.

8. A process according to claim 7, further comprising:

further obtaining gray balanced and color calibrated additional images of said cervix using said digital camera after application of said acetic acid.

9. A device for diagnosing cancer in a cervix, comprising:

a hand held digital camera for taking color calibrated and gray balanced digital color images of said cervix having known pixel sizes;

a digital processing platform operably connected to said digital camera for detecting and analyzing colposcopic features to extract features from said color images using image processing algorithms, wherein said image processing algorithms comprise (1) anatomy feature detection, (2) acetowhite feature detection and characterization, (3) vessel feature detection and characterization, (4) lesion margin feature detection and characterization, (5) examination adequacy calculation, and (6) tissue classification.

* * * * *